United States Patent
Kyakuno et al.

(10) Patent No.: US 11,940,408 B2
(45) Date of Patent: Mar. 26, 2024

(54) MEASURING DEVICE

(71) Applicant: YOKOGAWA ELECTRIC CORPORATION, Tokyo (JP)

(72) Inventors: Toshihiko Kyakuno, Tokyo (JP); Yukihisa Takayama, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 127 days.

(21) Appl. No.: 17/463,844

(22) Filed: Sep. 1, 2021

(65) Prior Publication Data

US 2022/0065813 A1    Mar. 3, 2022

(30) Foreign Application Priority Data

Sep. 3, 2020    (JP) ................ 2020-148520

(51) Int. Cl.
    *G01N 27/416*      (2006.01)

(52) U.S. Cl.
    CPC ..... *G01N 27/4163* (2013.01); *G01N 27/4166* (2013.01)

(58) Field of Classification Search
    CPC .......... G01N 27/4163; G01N 27/4166; G01N 27/283; G01N 33/182; G01N 27/38; G01N 27/4168; G01N 27/07
    See application file for complete search history.

(56) References Cited

U.S. PATENT DOCUMENTS

| | | | | |
|---|---|---|---|---|
| 2016/0349205 | A1* | 12/2016 | Stetter ............... | H04B 5/0062 |
| 2018/0321186 | A1* | 11/2018 | Looney .............. | G01N 27/122 |
| 2019/0331640 | A1* | 10/2019 | Kuwagata ........... | G01N 27/30 |

FOREIGN PATENT DOCUMENTS

| | | | |
|---|---|---|---|
| CN | 102959371 A | | 3/2013 |
| JP | H02154142 A | * | 6/1990 |
| JP | 2001091495 A | * | 4/2001 |
| JP | 2001349866 A | * | 12/2001 |
| JP | 2001349866 A | | 12/2001 |

(Continued)

OTHER PUBLICATIONS

Mihashi et al., English translation of JP 2016080573 A, 2016. (Year: 2016).*

(Continued)

*Primary Examiner* — Joshua L Allen
*Assistant Examiner* — Shizhi Qian
(74) *Attorney, Agent, or Firm* — Osha Bergman Watanabe & Burton LLP (57) ABSTRACT

A measuring device includes: a first electrode immersed in sample water stored in a measuring tank; a second electrode immersed in the sample water; and a controller that: causes a power source to flow a current through the sample water between the first electrode and the second electrode; detects, based on a first digital signal, an interruption whereby an analog signal fluctuates by no less than a predetermined value; and calculates, based on a second digital signal, a concentration of a measurement target in the sample water. The first digital signal is acquired by sampling the analog signal with a first sampling period. The analog signal is based on the current flowing through the sample water. The second digital signal is acquired by sampling the analog signal with a second sampling period that is longer than the first sampling period.

8 Claims, 5 Drawing Sheets

(56) References Cited

FOREIGN PATENT DOCUMENTS

| JP | 2004053548 A | * | 2/2004 | |
|---|---|---|---|---|
| JP | 2004053549 A | * | 2/2004 | |
| JP | 2004191197 A | | 7/2004 | |
| JP | 2006198334 A | * | 8/2006 | ........... A61B 5/0537 |
| JP | 2008164408 A | | 7/2008 | |
| JP | 2009168694 A | * | 7/2009 | |
| JP | 2009236787 A | * | 10/2009 | |
| JP | 2016080573 A | | 5/2016 | |
| JP | 2016080573 A | * | 5/2016 | |
| JP | 2018047260 A | | 3/2018 | |
| JP | 2018124130 A | * | 8/2018 | |
| JP | 2019115714 A | | 7/2019 | |

OTHER PUBLICATIONS

Kitamoto et al., English translation of JPH02154142A, 1990. (Year: 1990).*
Akazawa et al., English translation of JP 2001349866A, 2001 (Year: 2001).*
Kuwagata et al. , English translation of JP2009168694A, 2009. (Year: 2009).*

* cited by examiner

MEASURING DEVICE

BACKGROUND

Technical Field

The present invention generally relates to a measuring device.

Related Art

Conventionally, a measuring device that measures a chlorine concentration in sample water using an electrode that rotates in the sample water is known (for example, see patent literature 1).

PATENT LITERATURE

Patent Literature 1: JP 2008-164408 A

The measuring device calculates the chlorine concentration in the sample water by measuring a magnitude of a current at a predetermined timing in a state wherein a current is flowing through the sample water. The magnitude of the current flowing through the sample water may fluctuate regardless of the timing of measurement. Detecting fluctuations in the magnitude of the current flowing through the sample water is advantageous in understanding a state of the measuring device.

SUMMARY

One or more embodiments provide a measuring device whose state is easy to understand.

A measuring device according to one or more embodiments includes a control unit. The control unit detects, based on data from sampling by a first sampling period a signal based on a current flowing through sample water, an interruption whereby the signal fluctuates by no less than a predetermined value and calculates, based on data from sampling the signal by a second sampling period longer than the first sampling period, a concentration of a measurement target in the sample water. By doing so, the control unit can decrease only a computational count for calculating the concentration of the measurement target while executing the computation for detecting an interruption at a high frequency, and the control unit can decrease an overall computational burden. As a result, detection of a voltage fluctuation of an amount of time shorter than a period of calculating the concentration of the measurement target and mitigation of a computational burden are realized.

In a measuring device according to one or more embodiments, the control unit may generate the data sampled by the second sampling period by extracting one portion of the data sampled by the first sampling period. By doing so, data of two types of sampling periods are acquired by just one AD converter. As a result, detection of a voltage fluctuation of an amount of time shorter than a period of calculating the concentration of the measurement target and mitigation of a computational burden are realized by a simple configuration.

A measuring device according to one or more embodiments may be further provided with a first AD converter that samples the signal by the first sampling period and a second AD converter that samples the signal by the second sampling period. The control unit may acquire the data sampled by the first sampling period from the first AD converter and acquire the data sampled by the second sampling period from the second AD converter. By doing so, it is unnecessary for the second sampling period to be a natural-number multiple of the first sampling period. As a result, sampling periods can be determined freely.

In a measuring device according to one or more embodiments, the control unit may determine a preventive maintenance timing based on a comparison between a frequency of detected interruptions and a determination value. Doing so makes a maintenance timing of the measuring device easy to understand. As a result, a convenience of the measuring device 1 improves.

A measuring device according to one or more embodiments may be further provided with a first electrode that is immersed in the sample water and a motor that rotates the first electrode at a rotational velocity that can be changed by the control unit. By such a configuration, the measuring device can operate in various driving modes. As a result, a convenience of the measuring device improves.

In a measuring device according to one or more embodiments, the motor may rotate in a forward direction, this being either clockwise or counterclockwise, when the rotational velocity is a positive value and rotate in a reverse direction of the forward direction when the rotational velocity is a negative value. The control unit may control rotation of the motor so the rotational velocity changes alternatingly between a positive value and a negative value in a situation of operating in a measuring mode of calculating the concentration of the measurement target in the sample water. By doing so, the first electrode becomes less likely to be stretched in one direction. As a result, a life of the first electrode is extended. That is, a maintenance timing is postponed.

In a measuring device according to one or more embodiments, the control unit may control rotation of the motor so an absolute value of the rotational velocity in a situation of operating in a standby mode of not calculating the concentration of the measurement target in the sample water is less than an absolute value of the rotational velocity in a situation of operating in a measuring mode of calculating the concentration of the measurement target in the sample water. By doing so, the first electrode or a slip ring that is electrically connected to the rotating first electrode becomes less likely to be abraded. As a result, a life of the components is extended. That is, a maintenance timing is postponed.

In a measuring device according to one or more embodiments, the control unit may control the rotational velocity based on a magnitude of a current flowing through standard sample water having a known concentration of the measurement target. By doing so, an error in a calculation result of the concentration of the measurement target is reduced. As a result, a convenience of the measuring device improves.

According to one or more embodiments, a measuring device whose state is easy to understand is provided.

DETAILED DESCRIPTION

Figure 1:
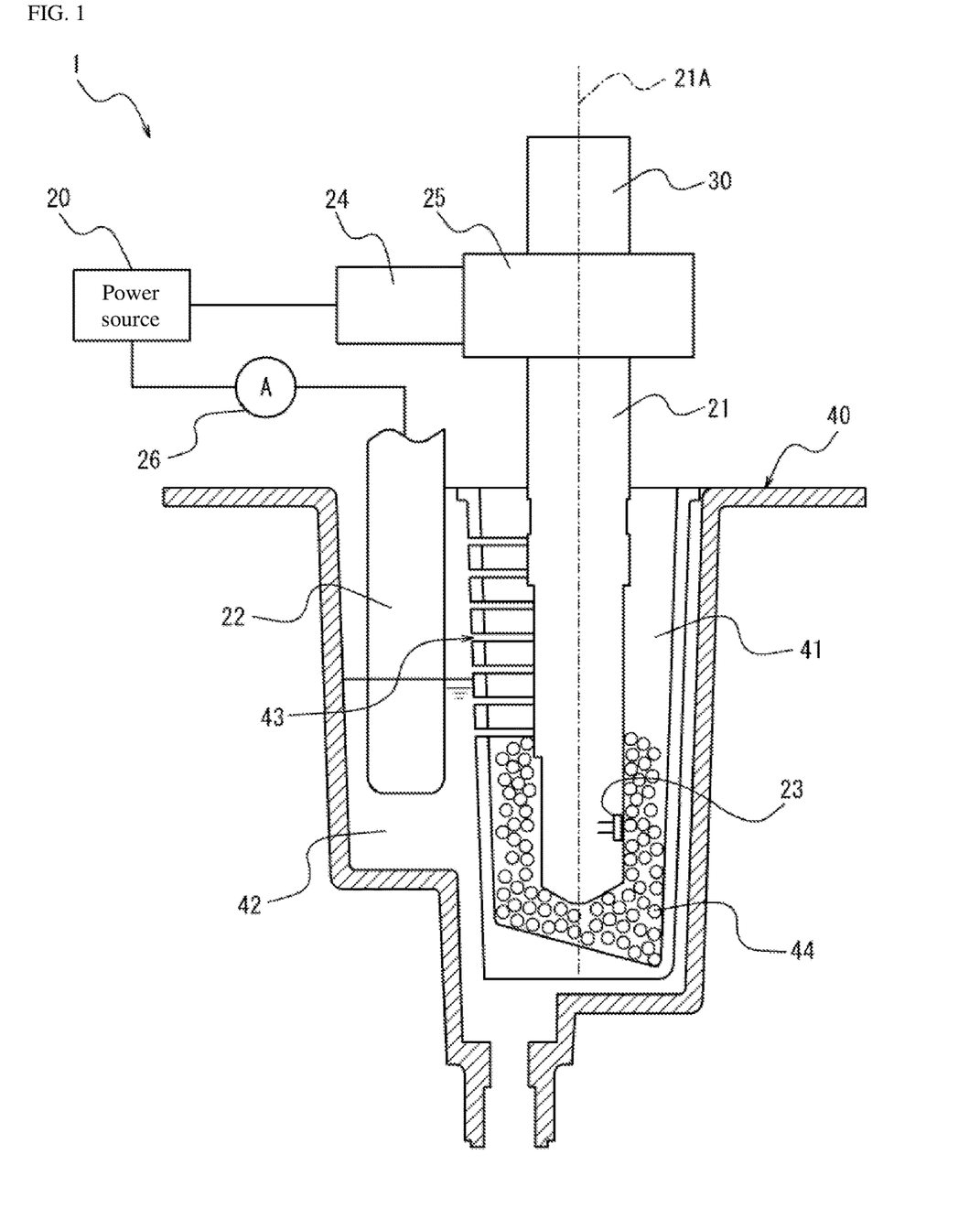
FIG. 1 is a sectional view illustrating a configuration example of a measuring device according to one or more embodiments.
Figure 2:
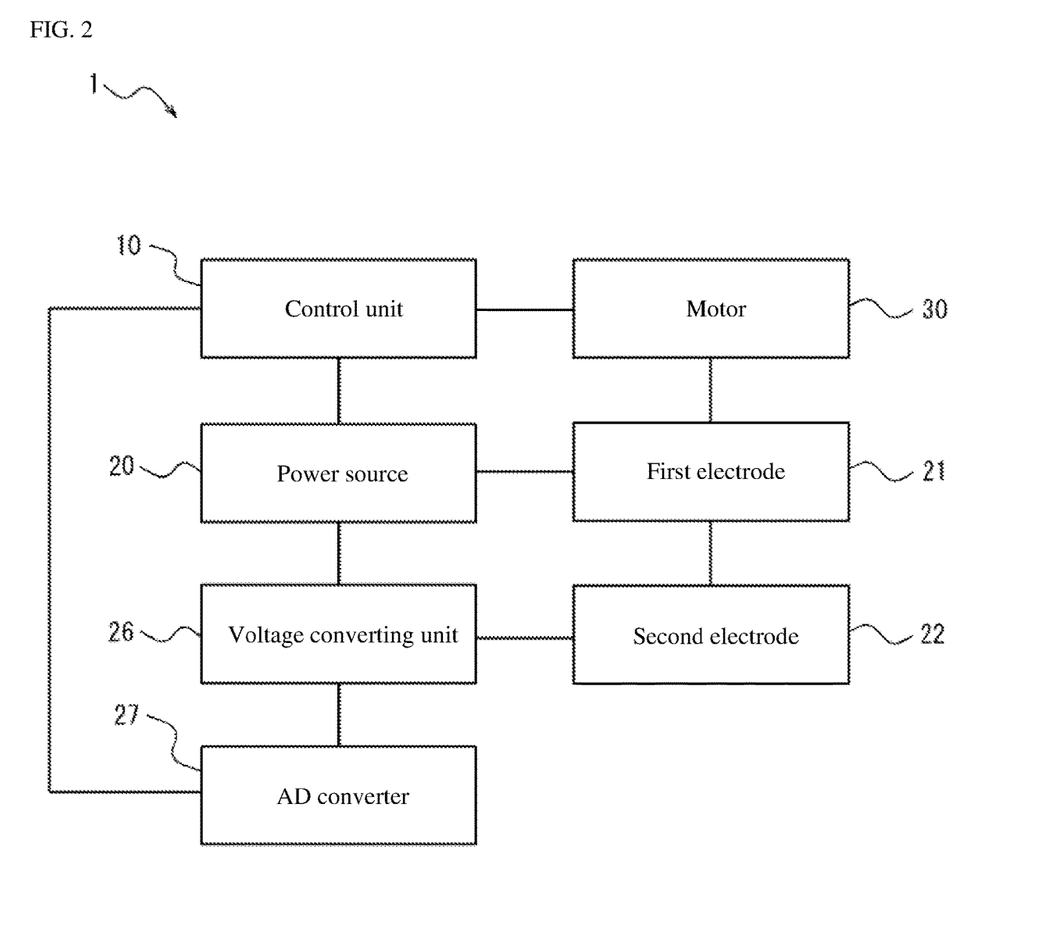
FIG. 2 is a block diagram illustrating the configuration example of the measuring device according to one or more embodiments.

In one or more embodiments, the measuring device 1 illustrated in FIG. 1 and FIG. 2 is described. The measuring device 1 performs sampling by applying a predetermined voltage to sample water into which an electrode is immersed and converting a current flowing through the sample water into a voltage and calculates a concentration of a measurement target in the sample water based on the sampled voltage. The measurement target may include, for example, chlorine, bromine, or iodine. The measurement target may include, for example, a metal ion.

The measuring device 1 according to one or more embodiments will be described below while being compared against a comparative example.

Comparative Example

A measuring device of a comparative example for the measuring device 1 according to one or more embodiments is described. The measuring device according to the comparative example calculates a chlorine concentration in sample water by measuring a voltage, converted from a current flowing through the sample water, by a predetermined sampling period.

Here, a state of the measuring device 1 can change due to various factors. The state of the measuring device 1 can be understood from fluctuations in the voltage converted from the current flowing through the sample water. The voltage may fluctuate in an amount of time shorter than the sampling period. A voltage fluctuation in a short amount of time can represent the state of the measuring device 1. The measuring device of the comparative example cannot detect a voltage fluctuation of an amount of time shorter than the sampling period, making it difficult to understand the state of the measuring device 1.

If the sampling period were simply shortened in the measuring device of the comparative example, although a voltage fluctuation of a short amount of time would be detected, calculating the chlorine concentration based on the sampled voltage would become an excessive burden. It is sought to realize detecting a voltage fluctuation of a short amount of time and mitigating this burden.

According to one or more embodiments, the measuring device 1 can detect a voltage fluctuation of a short amount of time and mitigate this burden.

(Configuration Example of Measuring Device 1 According to One or More Embodiments of Present Disclosure)

As illustrated in FIG. 1 and FIG. 2, a measuring device 1 according to one or more embodiments is provided with a measuring tank 40, which stores sample water, and a measuring unit that measures a characteristic of the sample water by flowing a current through the sample water. In one or more embodiments, the measuring device 1 measures a chlorine concentration in the sample water as the characteristic of the sample water. That is, in one or more embodiments, it is supposed that a measurement target is chlorine. The measurement target is not limited to chlorine and may be various other substances. The measuring unit is provided with a control unit 10 (controller), a power source 20, a voltage converting unit 26, an AD converter 27, a first electrode 21, and a second electrode 22.

The control unit 10 flows a current through the sample water through the first electrode 21 and the second electrode 22 by controlling the power source 20. The voltage converting unit 26 converts the current flowing through the sample water into a voltage. The AD converter 27 samples the voltage converted by the voltage converting unit 26. The control unit 10 acquires the sampled voltage from the AD converter 27 and calculates the chlorine concentration in the sample water based on the acquired voltage.

The control unit 10 may be configured by including a processor such as a CPU (central processing unit). The control unit 10 may realize a predetermined function by causing the processor to execute a predetermined program.

The measuring device 1 may be further provided with a storage unit. The storage unit may store various information used in an operation of the control unit 10, a program for realizing a function of the control unit 10, or the like. The storage unit may function as a work memory of the control unit 10. The storage unit may be constituted by, for example, a semiconductor memory. The storage unit may be included in the control unit 10 or be configured separately from the control unit 10.

The measuring device 1 may be further provided with an output unit. The output unit outputs information acquired from the control unit 10. Specifically, the output unit outputs the chlorine concentration in the sample water calculated by the control unit 10. The output unit may notify information to a user by outputting visual information such as characters, shapes, or images, directly or via an external device or the like. The output unit may be provided with a display device or have a wired or wireless connection to a display device. The display device may include various displays, such as a liquid-crystal display. The output unit may notify information to the user by outputting aural information such as audio, directly or via an external device or the like. The output unit may be provided with an audio output device such as a speaker or have a wired or wireless connection to an audio output device. The output unit may notify information to the user by outputting not only visual information or aural information but also information that the user can sense by another sense, directly or via an external device or the like. The output unit may be included in the control unit 10 or be configured separately from the control unit 10.

The first electrode 21 and the second electrode 22 are housed in the measuring tank 40 so as to be immersed in the sample water stored in the measuring tank 40. The power source 20 is connected in series between the first electrode 21 and the second electrode 22 and produces a potential difference between the first electrode 21 and the second electrode 22. By the power source 20 producing a potential difference between the first electrode 21 and the second electrode 22, a current flows through sample water positioned between the first electrode 21 and the second electrode 22.

The first electrode 21 has a main body and a working electrode 23. The main body is configured as a circular column and is inserted in the measuring tank 40. The main body is constituted by an insulator such as a resin. The working electrode 23 is positioned on a tip side (side inserted in the measuring tank 40) of the main body so as to be immersed in the sample water, and it flows a current through the sample water by contacting the sample water. The current flowing through the sample water flows to the first electrode 21 through the working electrode 23. The working electrode 23 is configured by including a metal such as gold (Au) or another conductive material. In one or more embodiments, it is supposed that the working electrode 23 is configured by including gold.

The voltage converting unit 26 is connected in series to a circuit connecting the first electrode 21, the second electrode 22, and the sample water; converts the current flowing through the sample water into a voltage; and outputs this. The voltage converted from the current flowing through the sample water is also referred to as a signal, which is an analog signal, based on the current flowing through the sample water. The voltage converting unit 26 may be configured by including, for example, a resistor. The voltage output by the voltage converting unit 26 is an analog signal. The AD converter 27 converts the analog signal of the voltage output by the voltage converting unit 26 into a digital signal by sampling the analog signal by a predetermined sampling period and outputs the digital signal to the control unit 10. The digital signal output by the AD converter 27 corresponds to a magnitude of the current flowing through the sample water.

The magnitude of the current flowing through the sample water is determined based on at least the chlorine concentration in the sample water. Therefore, the control unit 10 can calculate the chlorine concentration in the sample water based on the digital signal corresponding to the magnitude of the current flowing through the sample water. The digital signal corresponding to the magnitude of the current flowing through the sample water is acquired by the voltage converting unit 26 and the AD converter 27. The control unit 10 may calculate the chlorine concentration in the sample water based also on a magnitude of the potential difference produced between the first electrode 21 and the second electrode 22. The control unit 10 may calculate the chlorine concentration in the sample water based also on a shape of a portion immersed in the sample water of the first electrode 21 and the second electrode 22. The control unit 10 may generate a function or table of a calibration curve based on a measurement result of a current flowing through standard sample water having a known chlorine concentration. The control unit 10 may calculate the chlorine concentration in the sample water based on a measurement result of the current flowing through the sample water and a calibration curve.

The current flowing through the sample water is limited by a magnitude of a diffusion current that flows via the sample water between the working electrode 23 and the second electrode 22. The magnitude of the diffusion current is greatly affected by a state of a diffusion layer produced near a surface of the working electrode 23. Therefore, as the state of the diffusion layer becomes more stable, a measurement value of the voltage represented by the digital signal acquired by the voltage converting unit 26 and the AD converter 27 becomes more stable. The diffusion layer is formed by a concentration distribution of ions of the sample water near the surface of the working electrode 23. The concentration distribution of the ions of the sample water near the surface of the working electrode 23 is produced by a current flowing through the sample water. The state of the diffusion layer is stabilized by stabilizing the concentration distribution of the ions of the sample water near the surface of the working electrode 23.

The ion concentration distribution of the sample water near the surface of the working electrode 23 changes according to the diffusion current. By sample water positioned near the surface of the working electrode 23 being stably interchanged, the ion concentration distribution of the sample water near the surface of the working electrode 23 stabilizes to a steady state. The measuring device 1 stably interchanges the sample water near the surface of the working electrode 23 by rotating the first electrode 21 having the working electrode 23.

Therefore, the measuring unit is further provided with a motor 30 that rotates the first electrode 21. The first electrode 21 may be formed in a rod shape having a longitudinal direction. The motor 30 is connected to the first electrode 21 so the first electrode 21 rotates around a rotational axis 21A along the longitudinal direction of the first electrode 21. The motor 30 can rotate at a variable rotational velocity in a period wherein the measuring device 1 is in a started state. For example, the rotational velocity of the motor 30 can be raised and lowered. That is, the motor 30 is configured to be able to change its rotational velocity. The motor 30 can stop rotation by making the rotational velocity zero while the measuring device 1 is still in the started state. In one or more embodiments, the rotational velocity may be equivalent to a rotational speed, a rotational frequency or the like in the controlling of the motor.

The rotational velocity of the motor 30 affects the ion concentration distribution of the sample water near the surface of the working electrode 23. As a result, the rotational velocity of the motor 30 affects the magnitude of the diffusion current. Specifically, the higher the rotational velocity of the motor 30, the greater the diffusion current that flows through the sample water having the same chlorine concentration. By raising the rotational velocity of the motor 30, the measuring device 1 can increase the diffusion current and facilitate calculating the chlorine concentration, even when the chlorine concentration of the sample water is low. That is, the measuring device 1 can raise a detection sensitivity of the chlorine concentration by raising the rotational velocity of the motor 30.

Furthermore, the motor 30 can change a direction of rotation. Specifically, the motor 30 can rotate the first electrode 21 clockwise or counterclockwise when viewing the first electrode 21, along the longitudinal direction thereof, from the motor 30 and in a direction of the measuring tank 40. In one or more embodiments, clockwise and counterclockwise rotation of the first electrode 21 are respectively referred to as rotation in a forward direction and rotation in a reverse direction. A rotational velocity of when the first electrode 21 rotates in the forward direction is represented by a positive value. A rotational velocity of when the first electrode 21 rotates in the reverse direction is represented by a negative value.

As above, the rotational velocity of the motor 30 affects the magnitude of the diffusion current. However, the rotational direction of the motor 30 does not affect the magnitude of the diffusion current. When the rotational velocity of the motor 30 can become a negative value, the greater an absolute value of the rotational velocity of the motor 30, the greater the diffusion current.

The measuring unit is further provided with a slip ring 25 and a brush 24 so as to be electrically connected to the power source 20 even in a state wherein the first electrode 21 is rotating. The slip ring 25 rotates together with the first electrode 21 by being driven by the motor 30. The brush 24 is disposed so as to contact a cylindrical surface of the slip ring 25. The brush 24 is biased toward the slip ring 25 so as to continue to contact the slip ring 25 even while the slip ring 25 is rotating.

The measuring tank 40 is provided with a first electrode housing portion 41 that houses the first electrode 21 and a second electrode housing portion 42 that houses the second electrode 22. The measuring tank 40 stores the sample water in the first electrode housing portion 41 and the second electrode housing portion 42. The measuring tank 40 is further provided with a passage 43 wherethrough the sample water passes between the first electrode housing portion 41 and the second electrode housing portion 42. The measuring tank 40 is further provided with an inlet that accepts the sample water and an outlet that discharges the sample water.

As above, a diffusion current flows between the surface of the working electrode 23 and the sample water. Here, the magnitude of the diffusion current is determined based on a surface area of the working electrode 23. When dirt is adhered to the surface of the working electrode 23, an effective surface area whereby the diffusion current flows to the working electrode 23 decreases. That is, dirt on the surface of the working electrode 23 affects the magnitude of the diffusion current.

Therefore, so dirt on the surface of the working electrode 23 can be cleaned, the measuring device 1 rotates the first electrode 21 while causing the surface of the working electrode 23 to contact granular members 44 such as ceramic beads or glass beads. To cause the surface of the working electrode 23 to contact the granular members 44, the measuring tank 40 houses the granular members 44 together with the sample water in the first electrode housing portion 41. That is, the granular members 44 are positioned inside the measuring tank 40. By doing so, when the first electrode 21 is housed in the first electrode housing portion 41, the granular members 44 contact the working electrode 23. By rotating the first electrode 21 in a state wherein the granular members 44 are contacting the working electrode 23, the granular members 44 produce friction against the surface of the working electrode 23 and reduce dirt adhered to the surface of the working electrode 23. That is, the granular members 44 can clean the surface of the working electrode 23.

The surface of the working electrode 23 is cleaned by the granular members 44 but is also deformed and abraded due to the friction with the granular members 44. Deformation or abrasion of the surface of the working electrode 23 causes the diffusion current flowing via the sample water between the working electrode 23 and the second electrode 22 to become unstable.

For example, when the working electrode 23 is constituted by a metal, the working electrode 23 is stretched thin over a surface of the main body of the first electrode 21 due to the friction with the granular members 44. By the working electrode 23 being stretched, the surface area of the working electrode 23 changes. Moreover, by the working electrode 23 being abraded, the surface area of the working electrode 23 can become small. A change in the surface area of the working electrode 23 changes the magnitude of the diffusion current and causes the diffusion current to become unstable. As a result, a calculation precision of the chlorine concentration in the sample water decreases.

Furthermore, by the working electrode 23 being stretched, the working electrode 23 becomes thin and more likely to be peeled from the first electrode 21. When the working electrode 23 is about to be or is actually peeled from the first electrode 21, the diffusion current can suddenly change. That is, separation of the working electrode 23 causes the diffusion current to become unstable. As a result, a calculation precision of the chlorine concentration in the sample water decreases.

From the above, deformation or abrasion of the working electrode 23 causes the diffusion current to become unstable. Therefore, when the working electrode 23 is deformed or abraded, a need arises to replace the first electrode 21. As a result, deformation or abrasion of the surface of the electrode shortens a life of the first electrode 21.

(Operational Example of Detecting Voltage Fluctuation of Short Amount of Time)

As above, the measuring device 1 according to one or more embodiments calculates a chlorine concentration in sample water based on data from sampling, by a predetermined sampling period, a signal that is a conversion of a current flowing through the sample water into a voltage.

Figure 3:
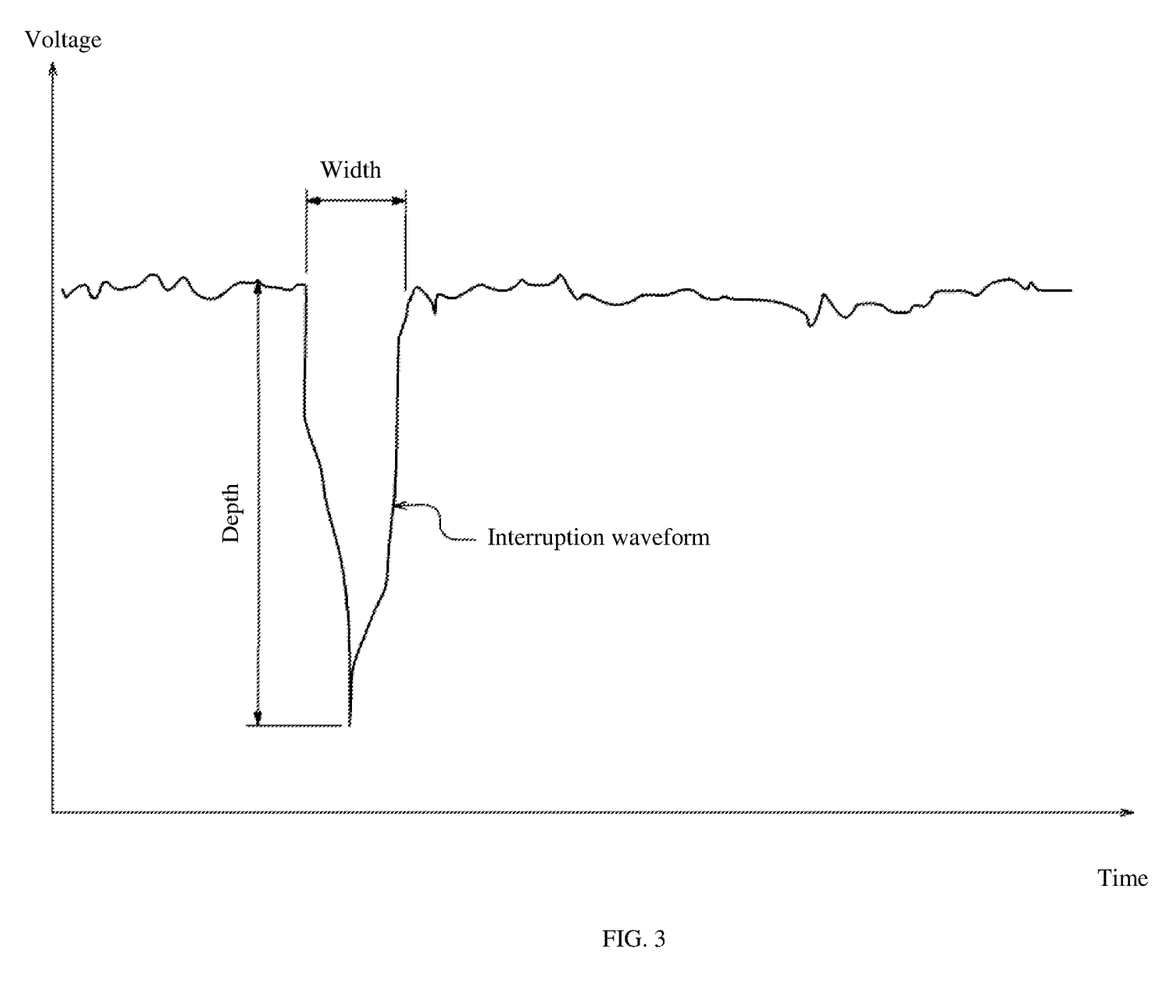
FIG. 3 is a graph illustrating one example of fluctuations over time in a voltage converted by a voltage converting unit.

Here, the voltage converted from the current flowing through the sample water may include a fluctuation that is represented by a spike-shaped waveform in the graph of voltage fluctuations over time illustrated in FIG. 3. The phenomenon that produces the spike-shaped waveform is also referred to as an interruption. The spike-shaped waveform is also referred to as an interruption waveform. The interruption waveform is represented by a falloff amount of the voltage and an amount of time for which the voltage falloff continues. The falloff amount of the voltage is also referred to as a depth. The amount of time for which the voltage falloff continues is also referred to as a width.

An interruption can occur in response to a change in a contact state between the slip ring 25 and the brush 24. For example, an interruption can occur when a contact resistance between the slip ring 25 and the brush 24 increases. An interruption can occur due to degradation of the slip ring 25 or the brush 24. That is, detecting interruption generation is useful in understanding a state of degradation of the slip ring 25 or the brush 24. By detecting interruption generation, the slip ring 25 or the brush 24 can be replaced or cleaned at an appropriate timing.

However, a voltage fluctuation due to an interruption occurs in an amount of time shorter than the predetermined sampling period. For example, a voltage fluctuation due to an interruption is generated for an amount of time on the order of 1 millisecond. Meanwhile, the predetermined sampling period of sampling the data for calculating the chlorine concentration is on the order of 1 second. Therefore, it is difficult to detect an interruption based on data sampled by the predetermined sampling period. As above, when the predetermined sampling period is simply shortened—for example, when the predetermined sampling period is shortened to an order of 1 millisecond—although it becomes possible to detect an interruption, a burden of calculating the chlorine concentration increases.

By, for example, operating as follows, the measuring device 1 according to one or more embodiments can realize detection of a voltage fluctuation of an amount of time shorter than a predetermined sampling period that is a period of calculating a chlorine concentration and mitigation of an overall burden including a burden of calculating the chlorine concentration.

<Calculation of Chlorine Concentration Based on One Portion of Sampled Data>

The control unit 10 acquires voltage data by sampling the magnitude of the current flowing through the sample water by a first sampling period. The control unit 10 extracts one data point from among the n sampled data points. Here, n is a natural number no less than 2. The control unit 10 calculates the chlorine concentration based on the extracted data point. In other words, to calculate the chlorine concentration in the sample water, the control unit 10 does not use all the data sampled by the first sampling period and uses one portion of the data.

The one data point extracted from the n data points corresponds to data sampled by a period n times greater than the first sampling period. That is, the one portion of the data used to calculate the chlorine concentration can also be referred to as data sampled by a second sampling period longer than the first sampling period. The control unit 10 can generate data sampled by the second sampling period by extracting one portion of data from the data sampled by the first sampling period. Then, based on the data sampled by the second sampling period longer than the first sampling period, the control unit 10 can calculate the chlorine concentration in the sample water.

Meanwhile, based on the data sampled by the first sampling period, the control unit 10 detects an interruption. The data sampled by the first sampling period may be indicated as a first digital signal acquired by sampling, with the first sampling period, an analog signal, which is based on the current flowing through sample water. The control unit 10 may determine that an interruption waveform has appeared when a falloff amount of the voltage becomes no less than a predetermined value. The control unit 10 may calculate a frequency of detecting an interruption. The frequency can be calculated as a number of interruption waveforms that appear per unit of time. The control unit 10 may calculate a width or a depth of an interruption waveform.

As above, the control unit 10 detects an interruption based on data sampled by a first sampling period and, while doing so, calculates a chlorine concentration in sample water based on data sampled by a second sampling period. The data sampled by a second sampling period may be indicated as a second digital signal acquired by sampling the analog signal, which is based on the current flowing through sample water, with the second sampling period. The second sampling period may be longer than the first sampling period. In other words, the control unit 10 extracts a part of samples of the first digital signal, and generates, based on the extracted part of samples, the second digital signal. A burden of a computation for detecting an interruption is lighter than a burden of a computation for calculating the chlorine concentration. Therefore, the control unit 10 can decrease an overall computational burden by decreasing only a computational count for calculating the chlorine concentration while executing the computation for detecting an interruption at a high frequency. As a result, detection of a voltage fluctuation of an amount of time shorter than a period of calculating the chlorine concentration and mitigation of a computational burden are realized.

Furthermore, by the control unit 10 generating data sampled by the second sampling period from data sampled by the first sampling period, the measuring device 1 can acquire data of two types of sampling periods by just one AD converter 27. As a result, detection of a voltage fluctuation of an amount of time shorter than a period of calculating the chlorine concentration and mitigation of a computational burden are realized by a simple configuration.

Furthermore, the control unit 10 may calculate the chlorine concentration in the sample water and detect an interruption based on the data sampled by the second sampling period. Moreover, the control unit 10 may detect an interruption and calculate the chlorine concentration in the sample water based on the data sampled by the first sampling period.

Figure 4:
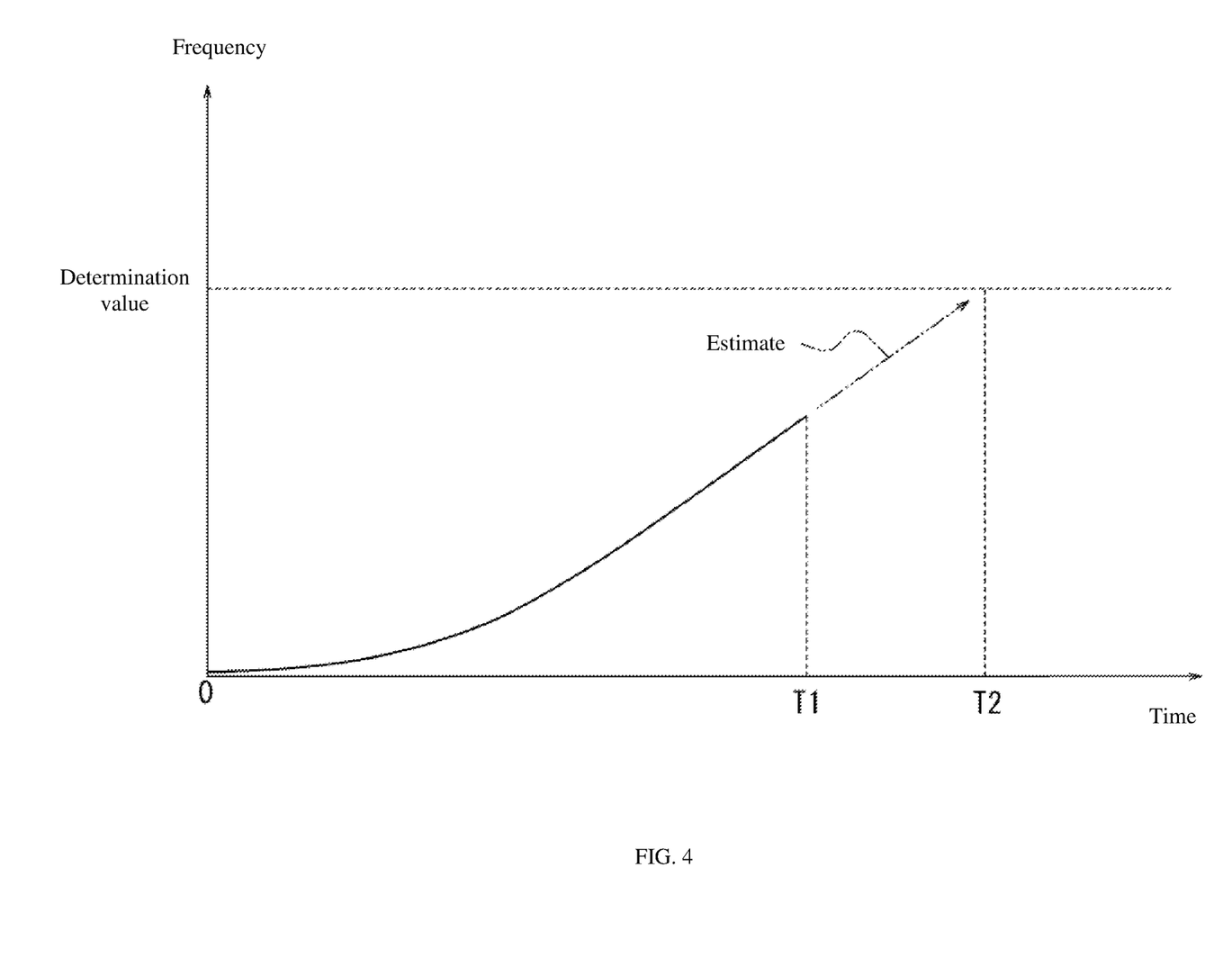
FIG. 4 is a graph illustrating one example of fluctuations over time in a frequency of detecting an interruption.

As illustrated in FIG. 4, the frequency of interruptions detected by the control unit 10 increases over time. When the frequency of interruptions reaches a determination value, the control unit 10 may determine that a state of the measuring device 1 is one wherein the slip ring 25 or the brush 24 needs maintenance. The control unit 10 may determine that the first electrode 21 of the measuring device 1 needs maintenance. Such a configuration makes a maintenance timing of the measuring device 1 easy to understand. As a result, a convenience of the measuring device 1 improves.

Furthermore, the control unit 10 may, at a time T1 prior to the frequency of interruptions reaching the determination value, estimate a subsequent change in the frequency of interruptions. In FIG. 4, the estimation result is represented by the dot-dot-dash arrow. The control unit 10 may calculate a time T2 whereat it is estimated that the frequency of interruptions reaches the determination value. Based on the calculation result of the control unit 10, an administrator of the measuring device 1 may plan to provide maintenance for the measuring device 1 at, for example, a time when the time T2 is reached or a time before or after the time T2. The timing for which maintenance of the measuring device 1 is planned is also referred to as a preventive maintenance timing. Moreover, the maintenance timing of the measuring device 1 becomes easy to understand. By maintenance of the measuring device 1 being planned in advance, an operational schedule of the measuring device 1 is established. As a result, a convenience of the measuring device 1 improves.

The control unit 10 may determine that the preventive maintenance timing has arrived at the point when the frequency of interruptions reaches the determination value. The control unit 10 may determine the timing of the estimated value of the frequency of interruptions reaching the determination value as the preventive maintenance timing. That is, the control unit 10 may determine the preventive maintenance timing based on a comparison between the frequency of interruptions and the determination value.

The control unit 10 may determine the preventive maintenance timing based on at least one among a depth or a width of an interruption.

<Sampling by Plurality of AD Converters 27>

Figure 5:
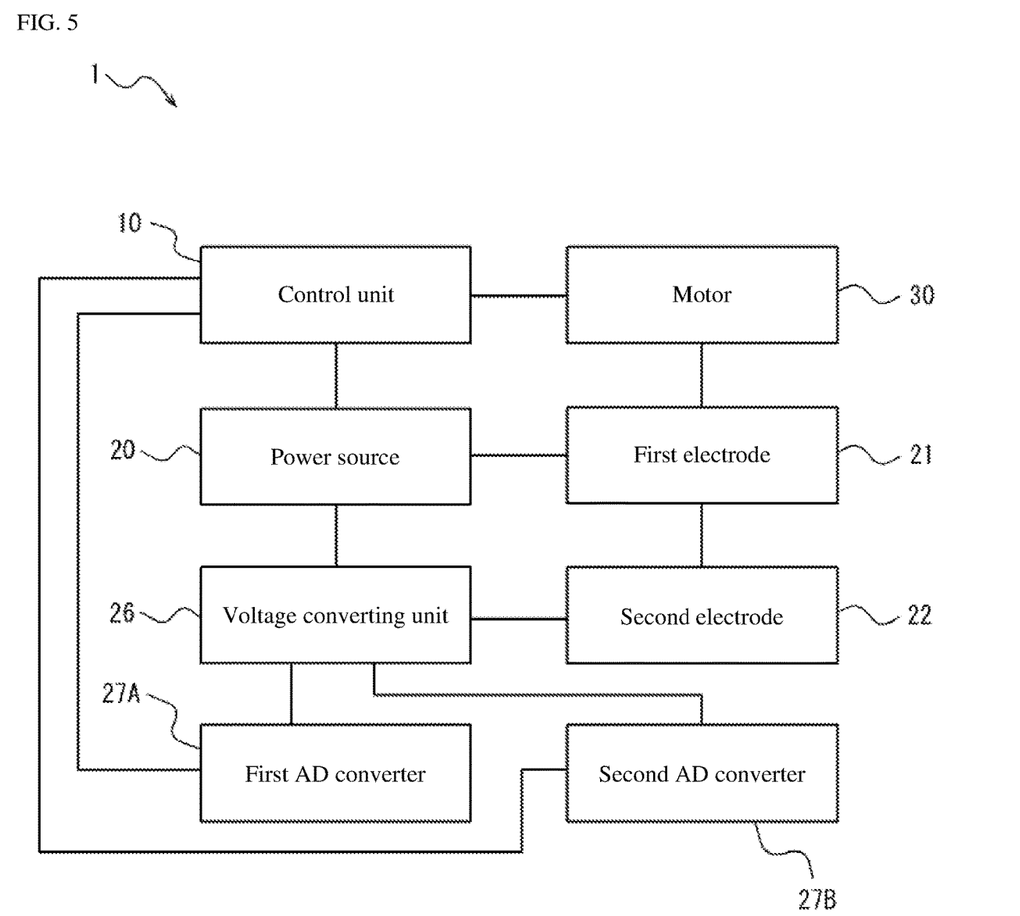
FIG. 5 is a block diagram illustrating another configuration example of the measuring device.

As illustrated in FIG. 5, the measuring device 1 may be provided with a first AD converter 27A and a second AD converter 27B instead of the AD converter 27 in FIG. 2. The first AD converter 27A outputs voltage data by sampling the current flowing through the sample water by the first sampling period. The second AD converter 27B outputs voltage data by sampling the current flowing through the sample water by the second sampling period. The control unit 10 monitors the state of the measuring device 1 based on the data acquired from the first AD converter 27A. The control unit 10 calculates the chlorine concentration in the sample water based on the data acquired from the second AD converter 27B. Such a configuration also realizes detection of a voltage fluctuation of an amount of time shorter than a sampling period of calculating a chlorine concentration and mitigation of a burden of calculating the chlorine concentration.

Furthermore, the first AD converter 27A and the second AD converter 27B can determine sampling periods independently. This makes it unnecessary for the second sampling period to be a natural-number multiple of the first sampling period. As a result, the measuring device 1 can determine sampling periods freely. Moreover, a convenience of the measuring device 1 improves.

As described above, the measuring device 1 according to one or more embodiments can vary a sampling period of acquiring data for detecting a voltage fluctuation and a sampling period of acquiring data for calculating a chlorine concentration in sample water. Such a configuration realizes detection of a voltage fluctuation of an amount of time shorter than a sampling period of calculating a chlorine concentration and mitigation of a burden of calculating the chlorine concentration. As a result, a convenience of the measuring device 1 improves.

(Operational Example that Extends Life of Components)

The measuring device 1 according to one or more embodiments can be improved in convenience by, for example, being operated as follows.

<Switching Between Measuring Mode and Standby Mode>

The control unit 10 continues to flow the diffusion current through the sample water when the measuring device 1 is in the started state. Meanwhile, the control unit 10 measures the diffusion current by a predetermined sampling period and calculates the chlorine concentration in the sample water. Said conversely, the control unit 10 does not measure the diffusion current other than at a timing determined by the predetermined sampling period. That is, the control unit 10 can switch an operation mode of the measuring device 1 between a measuring mode of measuring the diffusion current flowing through the sample water and a standby mode of not measuring the diffusion current.

As above, the rotational velocity of the motor 30 affects the magnitude of the diffusion current. Therefore, when operating in the measuring mode, the control unit 10 controls the rotational velocity of the motor 30 to a predetermined value for measurement. Meanwhile, when operating in the standby mode, the control unit 10 does not need to control the rotational velocity of the motor 30 to a predetermined value.

Here, the higher the rotational velocity of the motor 30, the easier it is for deformation or abrasion of the working electrode 23 of the first electrode 21 to advance. Moreover, the easier it is for abrasion of the slip ring 25 to advance.

<<Stoppage or Speed Reduction of Motor 30>>

Therefore, the control unit 10 of the measuring device 1 according to one or more embodiments may set the rotational velocity of the motor 30 to zero to stop rotation of the first electrode 21 when operating in the standby mode. Thus, deformation or abrasion of the working electrode 23 or abrasion of the slip ring 25 is less likely to advance. As a result, the life of each component is prolonged. Furthermore, when the first electrode 21 is made to continue to rotate in a state wherein supply of the sample water is stopped, a frictional force acting between the first electrode 21 and the granular members 44 becomes larger than when these are in water. As a result, the first electrode 21 is depleted quickly, and, depending on the situation, the first electrode 21 can fail. The measuring device 1 can reduce a risk of depletion or failure of the first electrode 21 by automatically stopping rotation of the motor 30 when a decrease of the sample water in the measuring tank 40 is sensed. Additionally, by automatically starting rotation of the motor 30 when supply of the sample water returns to normal, the measuring device 1 can realize intermittent measurement that conserves sample water. The measuring device 1 can sense whether the sample water is reduced or whether the sample water is present by fluctuating the voltage between the two electrodes and sensing a change in the current flowing between the two electrodes. The measuring device 1 may measure a resistance value between the two electrodes based on the change in current and determine whether the sample water is reduced or whether the sample water is present based on a measurement result of a magnitude of the resistance value.

When rotation of the first electrode 21 stops, the ion concentration distribution of the sample water near the surface of the working electrode 23—that is, the state of the diffusion layer—may deviate greatly from the steady state. In this situation, an amount of time from restarting rotation of the first electrode 21, so the measuring device 1 operates in the measuring mode, to the state of the diffusion layer near the surface of the working electrode 23 returning to the steady state can become prolonged. As a result, an amount of time for the measuring device 1 to return from operation in the standby mode to operation in the measuring mode and to return to a state of being able to restart measurement becomes prolonged.

Here, by not making the absolute value of the rotational velocity of the motor 30 zero, a degree to which the state of the diffusion layer deviates from the steady state is reduced compared to when the motor 30 is stopped. Thus, an amount of time for the state of the diffusion layer near the surface of the working electrode 23 to return to the steady state when returning the rotational velocity of the motor 30 to the rotational velocity of the situation of operating in the measuring mode is shortened. Therefore, the measuring device 1 can shorten the amount of time to return to operation in the measuring mode and extend the life of components by, when operating in the standby mode, making the absolute value of the rotational velocity of the motor 30 not zero but, instead, smaller than the absolute value of the rotational velocity of when operation is in the measuring mode. That is, the maintenance timing is postponed.

<<<Changing Rotational Direction of Motor 30>>>

When the rotational direction of the motor 30 is in a fixed direction, the surface of the working electrode 23 is stretched in the fixed direction by continuously receiving frictional force in the fixed direction from the granular members 44. Here, the measuring device 1 according to one or more embodiments may alternatingly change the rotational direction of the motor 30 between the forward direction and the reverse direction. By alternatingly changing the rotational direction of the motor 30, the direction of the frictional force received by the surface of the working electrode 23 is changed alternatingly. Thus, the surface of the working electrode 23 is no longer stretched only in one direction. Furthermore, the surface of the working electrode 23 can be pulled back in a reverse direction even if stretched in one direction. Thus, the surface area of the working electrode 23 becomes less likely to change. As a result, the magnitude of the diffusion current is stabilized. Furthermore, the working electrode 23 becomes less likely to be peeled off. As a result, the life of the first electrode 21 is prolonged. That is, the maintenance timing is postponed.

<Cleaning Mode>

The measuring device 1 may be dirtied by the sample water. Dirt adhered to the first electrode 21 and the second electrode 22 affects a detection precision of the chlorine concentration. Furthermore, although the first electrode 21 is less likely to be dirtied due to contact with the granular members 44, it is dirtied to a certain extent. Accordingly, the administrator of the measuring device 1 must clean the first electrode 21 and the like as appropriate. The measuring device 1 according to one or more embodiments may operate in a cleaning mode for cleaning the first electrode 21 and the like. When operating in the cleaning mode, the control unit 10 rotates the first electrode 21 by driving the motor 30 in a state wherein the first electrode 21 and the second electrode 22 are pulled up out of the measuring tank 40. By cleaning equipment such as a brush or a cloth being pressed against the first electrode 21 in a state wherein the first electrode 21 is rotating, the labor of cleaning the first electrode 21 can be reduced.

The control unit 10 may control the motor 30 such that the rotational velocity of the motor 30 when operating in the cleaning mode is different from the rotational velocity when operating in the measuring mode. Thus, rotation of the motor 30 can be controlled to a rotational velocity suitable for cleaning. As a result, dirt on the surface of the first electrode 21 can be efficiently removed. Concerning the rotational direction of the motor 30, when operating in at least one mode among the measuring mode and the cleaning mode, the control unit 10 may control rotation of the motor 30 so as to alternatingly change the rotational velocity of the motor 30 between a positive value and a negative value.

Furthermore, when operating in the cleaning mode, the control unit 10 may alternatingly switch the rotational direction of the motor 30 between the forward direction and the reverse direction. Thus, by simply pressing the cleaning equipment against the first electrode 21, it becomes easy to rub off dirt adhered to the first electrode 21 by a reciprocating motion. As a result, dirt on the surface of the first electrode 21 can be efficiently removed.

<Break-In Mode>

In the measuring device 1, the granular members 44 such as ceramic beads or glass beads in contact with the surface of the first electrode 21 are abraded by friction with the first electrode 21. That is, as a consumable, the granular members 44 are replaced as appropriate.

Here, immediately after replacement, the new granular members 44 have very fine surface projections like konpeito, to give an extreme example. The projections on the surface of the granular members 44 decrease as the first electrode 21 rotates and friction with the granular members 44 continues. As a result, the surface of the granular members 44 becomes smooth.

The surface state of the granular members 44, the frictional state between the first electrode 21 and the granular members 44, or the frictional state between the granular members 44 tends to undergo a comparatively large change in an initial stage of operation after replacement and to stabilize once operation continues for a certain extent. The more these states stabilize, the more the magnitude of the diffusion current and the calculation result of the chlorine concentration in the sample water stabilize. Conversely, the calculation result of the chlorine concentration in the sample water can drift until the surface state or the frictional state of the granular members 44 stabilizes.

Therefore, the measuring device 1 according to one or more embodiments operates in a break-in mode immediately after the replacement of the granular members 44. When operating in the break-in mode, the control unit 10 sets the rotational velocity of the motor 30 higher than the rotational velocity of when operation is in the measuring mode. The surface state or frictional state of the granular members 44 stabilizes as a number of rotations of the first electrode 21 increases. Accordingly, an amount of time until the state stabilizes is shortened by increasing the rotational velocity of the motor 30.

<Setting Rotational Velocity According to Environment>

The measuring device 1 may operate in an environment wherein dirt is less likely to adhere to the first electrode 21—for example, an environment wherein dirtying components that can adhere to the first electrode 21 are not abundant in the sample water. In such an environment, the measuring device 1 can set the rotational velocity of the motor 30 without considering removal of dirt adhering to the first electrode 21. Thus, the measuring device 1 can lower the rotational velocity of the motor 30. By lowering the rotational velocity of the motor 30 to lower the rotational velocity of the first electrode 21, deformation or abrasion of the first electrode 21 or abrasion of the slip ring 25 becomes less likely to advance. As a result, the life of each component is extended.

<Sensitivity Adjustment>

The magnitude of the diffusion current flowing in the working electrode 23 may vary according to individual differences in the working electrode 23 even in sample water of the same chlorine concentration. The diffusion current varying according to the individual differences in the working electrode 23 can cause differences in sensitivity. Therefore, the measuring device 1 may correct the sensitivity for each device by calibration. Calibration work may be performed at each timing of replacement with a different working electrode 23. Should the calibration work be performed by an erroneous operation, a measurement value of the measuring device 1 can become abnormal or have a large error.

Here, as described above, the higher the rotational velocity of the motor 30, the higher a detection sensitivity of the chlorine concentration. By changing the rotational velocity of the motor 30, the control unit 10 can compensate for the magnitude of the diffusion current, reduce individual differences in sensitivity of the measuring device 1, and thereby provide a fixed or stabilized sensitivity. Specifically, the control unit 10 calculates the chlorine concentration by measuring a current in standard sample water having a known chlorine concentration and sets the rotational velocity of the motor 30 so the calculation result matches the known chlorine concentration. The measuring device 1 stores this difference in the rotational-velocity setting using one representative device at a time of production and assigns such as a value unique to the first electrode 21. The measuring device 1 may store the setting value by installing an ID chip on the electrode. As long as it operates at the set rotational velocity, the first electrode 21 assigned a value can perform measurement at the same sensitivity even when installed in another residual chlorine meter. By reducing the sensitivity difference when replacing the electrode and simplifying calibration work, errors due to incorrect calibration can be reduced.

As described above, the measuring device 1 according to one or more embodiments can realize various operation modes by making the rotational velocity of the motor 30 rotating the first electrode 21 variable. Thus, extension of the life of the components, setting the detection sensitivity of the chlorine concentration, error reduction in the calculation result of the chlorine concentration, and the like are realized. As a result, a convenience of the measuring device 1 improves.

The measuring device 1 according to one or more embodiments described above measures the chlorine concentration in the sample water as the characteristic of the sample water. The measuring device 1 may be configured to be able to measure the chlorine concentration in the sample water by distinguishing between a free chlorine concentration and a combined chlorine concentration. Furthermore, the characteristic of the sample water is not limited to the chlorine concentration in the sample water, and the measuring device 1 can be configured to, for example, measure a metal ion concentration in the sample water. That is, the measuring device 1 can be configured as a metal ion concentration meter. When the measuring device 1 is configured as a metal ion concentration meter, the granular members 44 may or may not be used. Furthermore, the measuring device 1 can also be configured as a bromine meter that measures a bromine concentration in the sample water. Moreover, the measuring device 1 can also be configured as an iodine meter that measures an iodine concentration in the sample water.

The first electrode 21 may be formed in a disc shape having a central axis. In this situation, the motor 30 is connected to the first electrode 21 such that the first electrode 21 rotates around the central axis.

The measuring unit of the measuring device 1 according to one or more embodiments has been described as having the first electrode 21 and the second electrode 22. The measuring unit may further have a third electrode. The third electrode determines a potential to serve as a reference when applying a voltage to the first electrode 21 and the second electrode 22. The third electrode does not contribute to the current flowing through the sample water. Due to the measuring unit having the third electrode, the second electrode 22 leaches less readily.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1: measuring device, 10: control unit, 20: power source, 21: first electrode, 21A: rotational axis, 22: second electrode, 23: working electrode, 24: brush, 25: slip ring, 26: voltage converting unit, 27: AD converter, 27A: first AD converter, 27B: second AD converter, 30: motor, 40: measuring tank, 41: first electrode housing portion, 42: second electrode housing portion, 43: passage, 44: granular member

What is claimed is:

1. A measuring device, comprising:
   a first electrode immersed in sample water stored in a measuring tank;
   a second electrode immersed in the sample water;
   a controller that causes a power source to flow a current through the sample water between the first electrode and the second electrode;
   a slip ring disposed between the first electrode and the power source;
   a brush disposed to contact the slip ring;
   a converter that converts the current into an analog signal; and
   an AD converter that converts the analog signal into a digital signal by sampling the analog signal with a sampling period during a measuring mode in which a concentration of a measurement target in the sample water is calculated, wherein
   the controller during the measuring mode:
      detects, based on the digital signal, that one or more changes in the analog signal are equal to or greater than a predetermined value, wherein the one or more changes in the analog signal are each caused by a change in contact between the slip ring and the brush;
      extracts a part of samples of the digital signal; and
      calculates the concentration based on the extracted part of samples,
   the measuring device further comprising:
      a motor that rotates the first electrode at a rotational velocity that is changed by the controller,
   the controller operates in a standby mode where the concentration is not calculated, and
   when the controller operates in the standby mode, the controller controls the motor such that a first absolute value of the rotational velocity when operating in the standby mode is larger than zero and smaller than a second absolute value of the rotational velocity when operating in the measuring mode.

2. The measuring device according to claim 1, wherein the controller determines a preventive maintenance timing based on a comparison between a frequency of the detected one or more changes in the analog signal and a determination value.

3. The measuring device according to claim 1, wherein the motor:
   rotates either clockwise or counterclockwise as a forward direction when the rotational velocity is a positive value; and
   rotates in a direction opposite to the forward direction when the rotational velocity is a negative value, and
   the controller controls a rotation of the motor and causes the rotational velocity to be changed alternately between the positive value and the negative value when the controller operates in the measuring mode.

4. The measuring device according to claim 1, wherein the controller controls the rotational velocity based on a magnitude of a current flowing in a standard sample water having a known measurement target concentration.

5. A measuring device comprising:
   a first electrode immersed in sample water stored in a measuring tank;
   a second electrode immersed in the sample water;
   a controller that causes a power source to flow a current through the sample water between the first electrode and the second electrode;
   a slip ring disposed between the first electrode and the power source;
   a brush disposed to contact the slip ring;
   a converter that converts the current into an analog signal;
   a first AD converter that during a measuring mode in which a concentration of a measurement target in the sample water is calculated, samples the analog signal with a first sampling period and converts the analog signal into a first digital signal; and
   a second AD converter that during the measuring mode, samples the analog signal with a second sampling period longer than the first sampling period and converts the analog signal into a second digital signal, wherein
   the controller during the measuring mode:
      detects, based on the first digital signal, that one or more changes in the analog signal are equal to or greater than a predetermined value, wherein the one or more changes in the analog signal are each caused by a change in contact between the slip ring and the brush; and
      calculates, based on the second digital signal, the concentration,
   the measuring device further comprises a motor that rotates the first electrode at a rotational velocity that is changed by the controller,
   the controller operates in a standby mode where the concentration is not calculated, and
   when the controller operates in the standby mode, the controller controls the motor such that a first absolute value of the rotational velocity when operating in the standby mode is larger than zero and smaller than a second absolute value of the rotational velocity when operating in the measuring mode.

6. The measuring device according to claim 5, wherein the controller determines a preventive maintenance timing based on a comparison between a frequency of the detected one or more changes in the analog signal and a determination value.

7. The measuring device according to claim 5, wherein the motor:
- rotates either clockwise or counterclockwise as a forward direction when the rotational velocity is a positive value; and
- rotates in a direction opposite to the forward direction when the rotational velocity is a negative value, and the controller controls a rotation of the motor and causes the rotational velocity to be changed alternately between the positive value and the negative value when the controller operates in the measuring mode.

8. The measuring device according to claim 5, wherein the controller controls the rotational velocity based on a magnitude of a current flowing in a standard sample water having a known measurement target concentration.

* * * * *